(12) United States Patent
Chilkoti

(10) Patent No.: US 8,334,257 B2
(45) Date of Patent: Dec. 18, 2012

(54) METHODS AND COMPOSITIONS FOR DELIVERING ACTIVE AGENTS WITH ENHANCED PHARMACOLOGICAL PROPERTIES

(75) Inventor: Ashutosh Chilkoti, Durham, NC (US)

(73) Assignee: Duke University, Durham, NC (US)

( * ) Notice: Subject to any disclaimer, the term of this patent is extended or adjusted under 35 U.S.C. 154(b) by 563 days.

(21) Appl. No.: 12/158,190

(22) PCT Filed: Dec. 20, 2006

(86) PCT No.: PCT/US2006/048572
§ 371 (c)(1),
(2), (4) Date: Sep. 2, 2008

(87) PCT Pub. No.: WO2007/073486
PCT Pub. Date: Jun. 28, 2007

(65) Prior Publication Data
US 2009/0004104 A1  Jan. 1, 2009

Related U.S. Application Data

(60) Provisional application No. 60/751,896, filed on Dec. 20, 2005.

(51) Int. Cl.
*A61K 38/22* (2006.01)
*A61K 38/39* (2006.01)

(52) U.S. Cl. ....... 514/13.1; 530/350; 530/353; 514/21.2

(58) Field of Classification Search .................. None
See application file for complete search history.

(56) References Cited

U.S. PATENT DOCUMENTS

| | | |
|---|---|---|
| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,749,647 A | 6/1988 | Thomas et al. |
| 4,752,638 A | 6/1988 | Nowinski et al. |
| 4,783,523 A | 11/1988 | Urry et al. |
| 4,870,055 A | 9/1989 | Urry et al. |
| 4,898,926 A | 2/1990 | Urry |
| 5,147,855 A | 9/1992 | Gozes et al. |
| 5,235,041 A | 8/1993 | Cappello et al. |
| 5,236,904 A | 8/1993 | Gerstenberg et al. |
| 5,243,038 A | 9/1993 | Ferrari et al. |
| 5,288,514 A | 2/1994 | Ellman |
| 5,445,934 A | 8/1995 | Fodor et al. |
| 5,447,912 A | 9/1995 | Gerstenberg et al. |
| 5,496,712 A | 3/1996 | Cappello et al. |
| 5,514,581 A | 5/1996 | Ferrari et al. |
| 5,519,004 A | 5/1996 | Urry |
| 5,520,672 A | 5/1996 | Urry |
| 5,527,610 A | 6/1996 | Urry |
| 5,545,617 A | 8/1996 | Dartt et al. |
| 5,624,711 A | 4/1997 | Sundberg et al. |
| 5,641,648 A | 6/1997 | Ferrari et al. |
| 5,681,816 A | 10/1997 | Korman |
| 5,700,914 A * | 12/1997 | Jorgensen et al. ............ 530/412 |
| 5,702,717 A | 12/1997 | Cha et al. |
| 5,747,646 A | 5/1998 | Hakimi et al. |
| 5,770,570 A | 6/1998 | Paul et al. |
| 5,770,697 A | 6/1998 | Ferrari et al. |
| 5,773,249 A | 6/1998 | Cappello et al. |
| 5,816,259 A | 10/1998 | Rose |
| 5,830,713 A | 11/1998 | Ferrari et al. |
| 5,854,387 A | 12/1998 | Urry et al. |
| 5,900,405 A | 5/1999 | Urry |
| 5,958,881 A | 9/1999 | Korman |
| 5,972,406 A | 10/1999 | Urry et al. |
| 5,972,883 A | 10/1999 | Gozes et al. |
| 5,998,588 A | 12/1999 | Hoffman et al. |
| 6,004,782 A | 12/1999 | Daniell et al. |
| 6,018,030 A | 1/2000 | Ferrari et al. |
| 6,037,321 A | 3/2000 | Cox et al. |
| 6,063,061 A | 5/2000 | Wallace et al. |
| 6,140,072 A | 10/2000 | Ferrari et al. |
| 6,153,655 A | 11/2000 | Martinez et al. |
| 6,184,348 B1 | 2/2001 | Ferrari et al. |
| 6,200,598 B1 | 3/2001 | Needham |
| 6,258,562 B1 | 7/2001 | Salfield et al. |
| 6,328,996 B1 | 12/2001 | Urry |
| 6,329,209 B1 | 12/2001 | Wagner et al. |
| 6,355,776 B1 | 3/2002 | Ferrari et al. |

(Continued)

FOREIGN PATENT DOCUMENTS

| | | |
|---|---|---|
| EP | 0449592 B1 | 11/1994 |
| WO | WO 86/06492 A1 | 11/1986 |
| WO | WO 96/32406 A1 | 10/1996 |
| WO | WO 99/11661 A1 | 3/1999 |
| WO | WO 00-56774 | 9/2000 |
| WO | WO 03/041393 | 5/2003 |
| WO | WO 2006-001806 A2 | 1/2006 |
| WO | WO 2006-078629 A2 | 7/2006 |
| WO | WO 2006/110292 | 10/2006 |
| WO | WO 2007/103515 A2 | 9/2007 |
| WO | WO 2007/104493 A1 | 9/2007 |
| WO | WO 2008-030968 A2 | 3/2008 |
| WO | WO 2008/141786 | 11/2008 |
| WO | WO 2008/155134 A1 | 12/2008 |
| WO | WO 2009/059278 A1 | 5/2009 |
| WO | WO 2010/042997 A1 | 4/2010 |

OTHER PUBLICATIONS

Dreher et al. ("Evaluation of an elastin-like polypeptide-doxorubicin conjugate for cancer therapy," J. Controlled Release, 2003, 91, 31-43).*

(Continued)

*Primary Examiner* — Christina Bradley
(74) *Attorney, Agent, or Firm* — Cooley LLP

(57) ABSTRACT

Provided herein are methods of enhancing in vivo efficacy of an active agent, comprising: administering to a subject an active agent that is coupled to a bioelastic polymer or elastin-like peptide, wherein the in vivo efficacy of the active agent is enhanced as compared to the same active agent when administered to the subject not coupled to (or not associated with) a bioelastic polymer or ELP.

6 Claims, 10 Drawing Sheets

U.S. PATENT DOCUMENTS

| | | | |
|---|---|---|---|
| 6,380,154 B1 | 4/2002 | Cappello et al. | |
| 6,429,188 B1 | 8/2002 | Perez et al. | |
| 6,503,534 B1 | 1/2003 | Pellet et al. | |
| 6,537,521 B2 | 3/2003 | Uzgiris | |
| 6,541,033 B1 | 4/2003 | Shah | |
| 6,582,926 B1 | 6/2003 | Chilkoti | |
| 6,593,394 B1 | 7/2003 | Li et al. | |
| 6,699,294 B2 | 3/2004 | Urry | |
| 6,852,834 B2 | 2/2005 | Chilkoti | |
| 6,998,387 B1 | 2/2006 | Goke et al. | |
| 7,084,243 B2 | 8/2006 | Glaesner et al. | |
| 7,094,755 B2 | 8/2006 | Burman et al. | |
| 7,101,843 B2 | 9/2006 | Glaesner et al. | |
| 7,138,486 B2 | 11/2006 | Habener et al. | |
| 7,141,547 B2 | 11/2006 | Rosen et al. | |
| 7,144,863 B2 | 12/2006 | DeFelippis et al. | |
| 7,176,278 B2 | 2/2007 | Prior | |
| 7,226,910 B2 | 6/2007 | Wilson et al. | |
| 7,232,879 B2 | 6/2007 | Galloway et al. | |
| 7,259,233 B2 | 8/2007 | Dodd et al. | |
| 7,271,149 B2 | 9/2007 | Glaesner et al. | |
| 7,332,473 B2 | 2/2008 | Onoue et al. | |
| 7,364,859 B2 | 4/2008 | Chilkoti | |
| 7,429,458 B2 | 9/2008 | Chilkoti | |
| 7,442,680 B2 | 10/2008 | Yong et al. | |
| 7,459,441 B2 | 12/2008 | Minagawa et al. | |
| 7,468,353 B2 | 12/2008 | Bevec | |
| 7,566,691 B2 | 7/2009 | Nestor | |
| 7,723,472 B2 | 5/2010 | Szoka | |
| 7,776,815 B2 | 8/2010 | Vanderby et al. | |
| 2001/0034050 A1* | 10/2001 | Chilkoti | 435/183 |
| 2002/0151458 A1 | 10/2002 | Gomariz et al. | |
| 2003/0059840 A1 | 3/2003 | Chilkoti | |
| 2003/0059841 A1 | 3/2003 | Chilkoti | |
| 2004/0063631 A1 | 4/2004 | Block | |
| 2004/0110296 A1 | 6/2004 | Vargeese et al. | |
| 2004/0234609 A1 | 11/2004 | Collier et al. | |
| 2005/0118109 A1 | 6/2005 | Block et al. | |
| 2005/0203009 A1 | 9/2005 | Pan et al. | |
| 2005/0255554 A1 | 11/2005 | Chilkoti | |
| 2006/0247156 A1 | 11/2006 | Vanderby et al. | |
| 2007/0009602 A1 | 1/2007 | Setton et al. | |
| 2008/0108573 A1 | 5/2008 | Duggan | |
| 2008/0207492 A1 | 8/2008 | Polt et al. | |
| 2008/0221041 A1 | 9/2008 | Block et al. | |
| 2008/0261863 A1 | 10/2008 | Whelan et al. | |
| 2008/0274961 A1 | 11/2008 | Bevec | |
| 2008/0318865 A1 | 12/2008 | Juul-Mortensen | |
| 2009/0005315 A1 | 1/2009 | Duggan | |
| 2009/0092582 A1 | 4/2009 | Bogin et al. | |
| 2009/0175821 A1 | 7/2009 | Bridon et al. | |
| 2009/0270317 A1 | 10/2009 | Chilkoti | |
| 2010/0016212 A1 | 1/2010 | Rubin et al. | |
| 2010/0022455 A1 | 1/2010 | Chilkoti | |
| 2010/0184651 A1 | 7/2010 | Maithal et al. | |
| 2011/0039776 A1 | 2/2011 | Chilkoti | |

OTHER PUBLICATIONS

Simoncsits et al. "Synthesis, cloning and expression in *Escherichia coli* of artificial genes coding for biologically active elongated precursors of the vasoactive intestinal polypeptide," Eur. J. Biochem., 1988, 178, 343-350).*

International Search Report and Written Opinion, PCT/US06/48572, date of mailing May 9, 2008.

Meyer et al. "Purification of Recombinant Proteins by Fusion with Thermally-Responsive Polypeptides", Natur Biotechnology, 1999, vol. 17, pp. 1112-1115.

Meyer et al., "Protein Purification by Fusion with an Environmentally Responsive Elastin-Like Polypeptide: Effect of Polypeptide Length on the Purification of Thioredoxin", Biotechnology Progress, 2001, vol. 17, pp. 720-728.

Chow et al., "Ultra-High Expression of a Thermally Responsive Recombinant Fusion Protein in *E. coli*", Biotechnology Progress, 2006, vol. 22, pp. 638-646.

Bidwell et al., "Application of thermally responsive polypeptides directed against c-Myc transcriptional function for cancer therapy," Mol. Cancer Ther. 4(7):1076-1085 (2005).

Chen et al., "A new temperature-and pH-responsive copolymer for possible use protein conjugation," Macromol. Chem. Phys. 196:1251-1259 (1995).

Chilkoti et al., "Targeted drug delivery by thermally responsive polymers," Adv. Drug Deliv. Rev. 54:613-630 (2002).

Chilkoti, A., "Biomedical Applications of Genetically Encoded Elastin Biopolymers," Abstracts of Papers, 222nd ACS National Meeting, Chicago, IL, US, Aug. 26-30, 2001, MACR-019, see abstract.

Chilkoti, A., et al., "Site-Specific Conjugation of a Temperature-Sensitive Polymer to a Genetically-Engineered Protein," Bioconjugate Chemistry, vol. 5, pp. 504-507, (1994).

Kobatake, Eiry et al., "Design and Gene Engineering Synthesis of an Extremely Thermostable Protein with Biological Activity," Biomacromolecules 2000, 1:382-386.

McPherson et al., "Product Purification by Reversible Phase Transition Following *Escherichia coli* Expression of Genes Encoding up to 251 Repeats of the Elastomeric Pentapeptide GVGVP," Protein Expression and Purification, 7, pp. 51-57, (1996).

McPherson, D. et al., "Production and purification of a recombinant elastomeric polypeptide, G-(VPGVG)19-VPGV from *Eschericia coli*," Biotechnol. Prog., 8:347-352 (1992).

Meyer et al., "Polypeptide Fusion Tag for Thermal Purification of Recombinant Proteins," Abstracts of Papers, 217th ACS National Meeting, Anaheim, CA, US, Mar. 21-25, 1999, BIOT-078, see abstract.

Meyer, Dan E. et al., "Drug targeting using thermally responsive polymers and local hyperthermia," Journal of Controlled release Jul. 6, 2001; 74:213-24.

Meyer, Dan E. et al., "Targeting a Genetically Engineered Elastin-like Polypeptide to Solid Tumors by Local Hypothermia," Cancer Res. Feb. 15, 2001; 61(4): 1548-54.

Nilsson, B. et al., "Fusion proteins in biotechnology and structural biology," Curr. Opin. Struct. Biol., 2:569-575 (1992).

Nilsson, J. et al., "Affinity Fusion Strategies for Detection, Purification and Immobilization of Recombinant Proteins," Protein Expression and Purification, 11:1-16 (1997).

Urry, D.W. et al., "Temperature of Polypeptide Inverse Temperature Transition Depends on Mean Residue Hydrophobicity," J. Am. Checm. Soc., 113:4346-4348 (1991).

Urry, D.W., "Entropic Elastic Processes in Protein Mechanisms, I. Elastic Structure Due to an Inverse Temperature Transition and Elasticity Due to Internal Chain Dynamics," Journal of Protein Chemistry, vol. 7, No. 1, pp. 1-34 (1988).

Urry, D.W., "Free Energy Transduction in Polypeptides and Proteins Based on Inverse Temperature Transitions," Prog. Biophys. Molec. Biol., vol. 57, pp. 23-57, (1992).

Urry, D.W., "Physical Chemistry of Biological Free Energy Transduction as Demonstrated by Elastic Protein-Based Polymers," J. Phys. Chem. B., vol. 101, No. 51, pp. 11007-11028, (1997).

Suzuki, et al., Encapsulation of VIP into liposomes restores vasorelaxation in hypertension in situ, Am. J. Physiol. 271(40):H282-H287 (1996).

Önyüksel et al., Human VIP-α: A long-acting, biocompatible and biodegradable peptide nanomedicine for essential hypertension, Peptides 27:2271-2275 (2006).

Onyiiksel, et al. A Novel Formulation of VIP in Sterically Stabilized Micelles Amplifies Vasodilation In Vivo, *Pharmaceutical Research*, vol. 16, No. 1, 1999.

Rubinstein, et al. Intratracheal and subcutaneous liposomal VIP normalizes arterial pressure in spontaneously hypertensive hamsters, International Journal of Pharmaceutics 316 (2006) 144-147.

Sejourne, et al. Development of a Novel Bioactive Formulation of Vasoactive Intestinal Peptide in Sterically Stabilized Liposomes, *Pharmaceutical Research*, vol. 14, No. 3, 1997.

\* cited by examiner

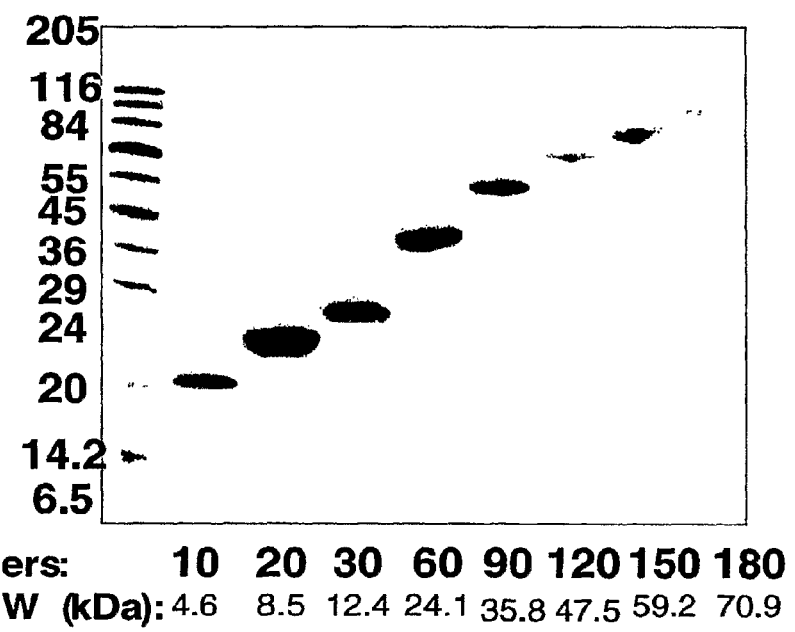
Figure 1. SDS-PAGE of a library of ELPs that are polymerized at the gene level, expressed in *E. coli*, and purified by exploiting the phase transition of the ELPs.

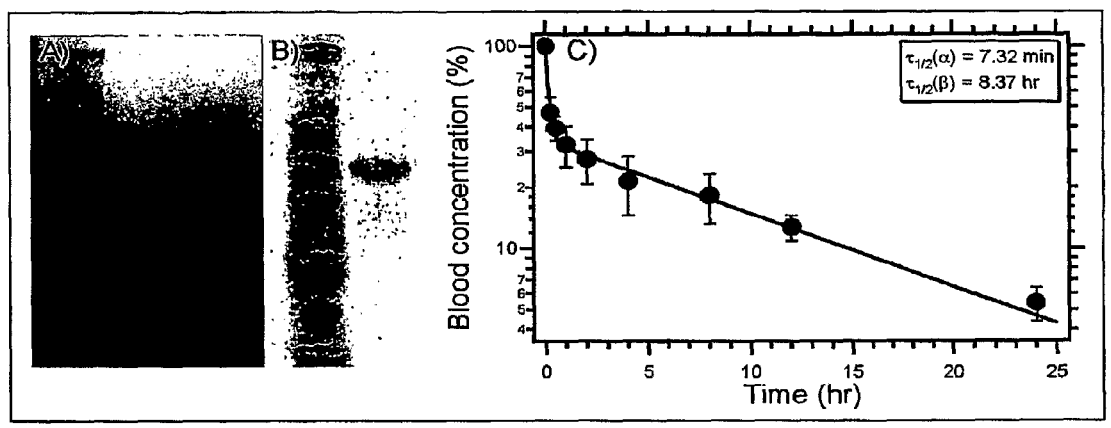
Figure 2. SDS-PAGE analysis of (A) $^{14}$C-ELP visualized by copper staining, (B) $^{14}$C-ELP autoradiography after SDS-PAGE. (C) Pharmacokinetic analysis of $^{14}$C-ELP in mice (Balb/c nu/nu) exhibits a characteristic distribution and elimination response with a terminal half-life of 8.4 hr.

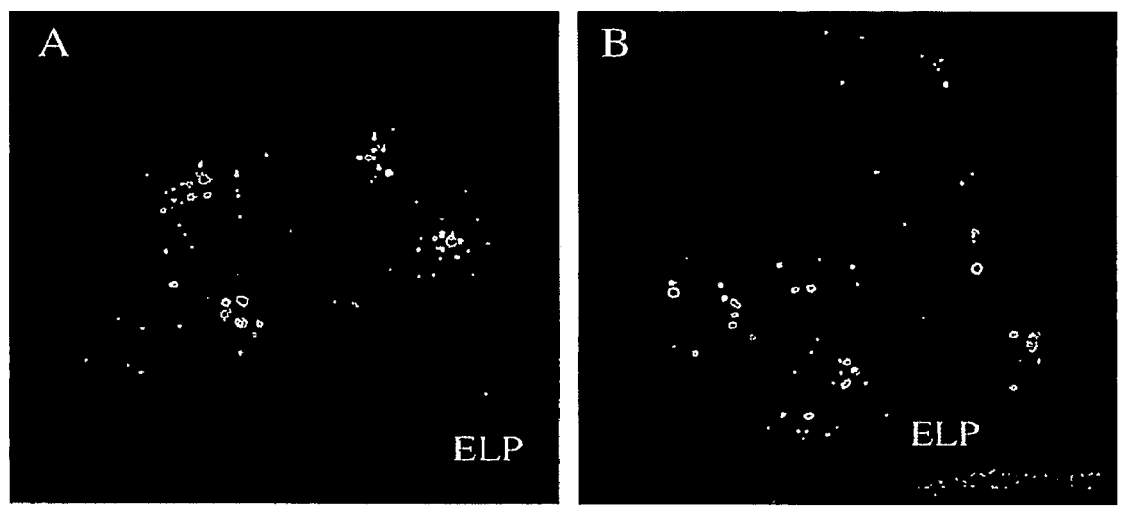
Figure 3. Uptake and localization of an ELP.

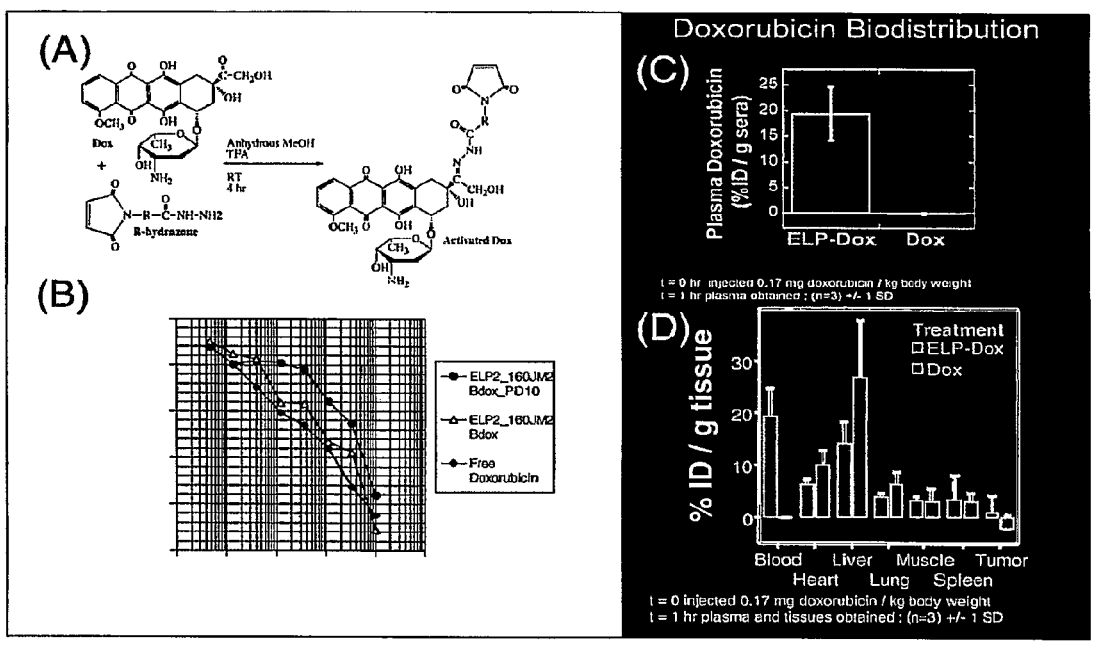
Figure 4. (A) Synthesis of a derivative with a terminal maleimide, (B) Example of cytotoxicity of Doxorubicin conjugated to ELP2-160JM2 conjugate (C) and (D) the biodistribution of Doxorubicin

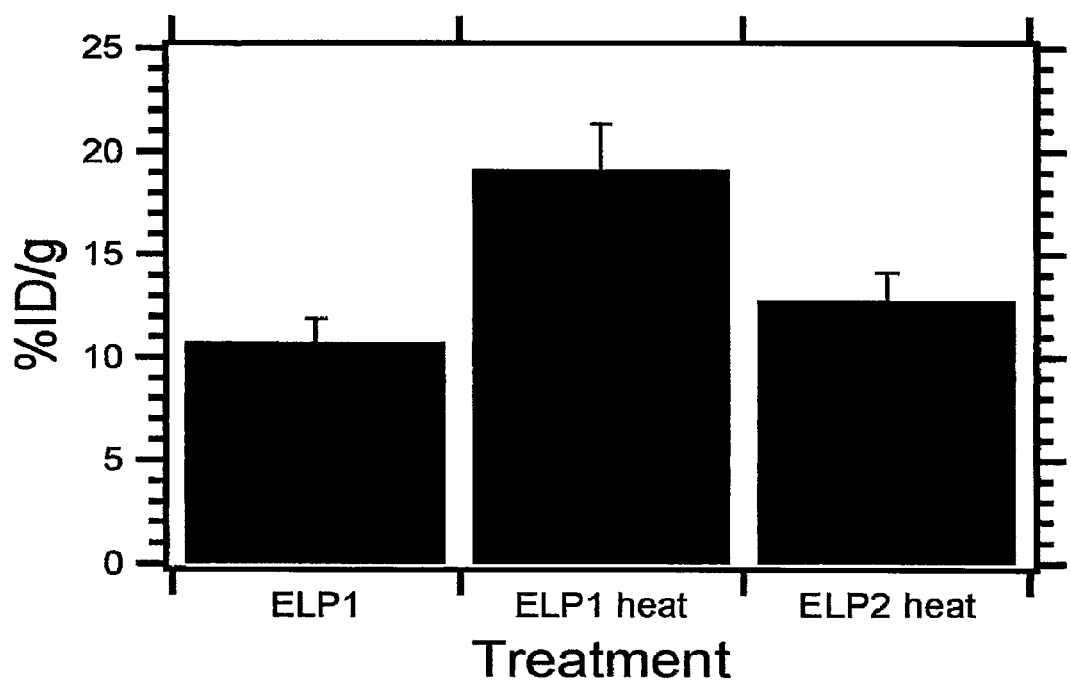
Figure 5. Accumulation of $^{14}$C-labeled ELPs in tumors.

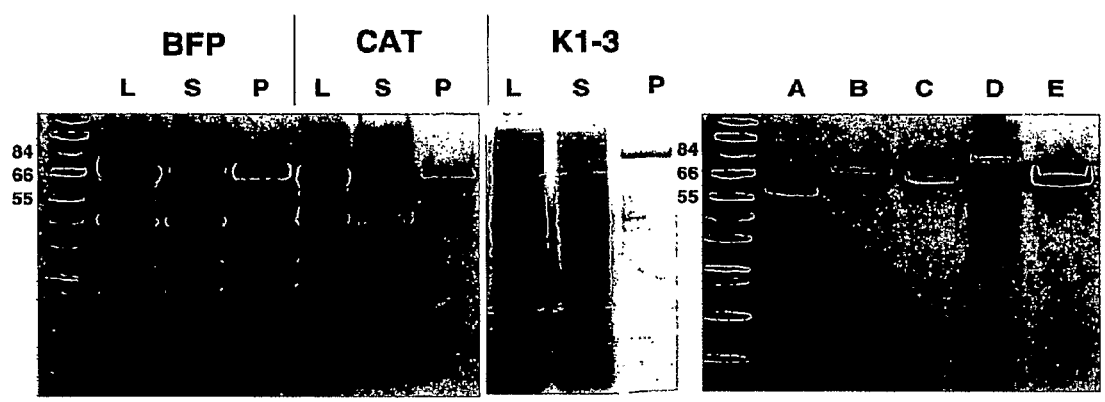
Figure 6. Expression of different ELP fusion proteins as examples of recombinant ELP-protein conjugates.

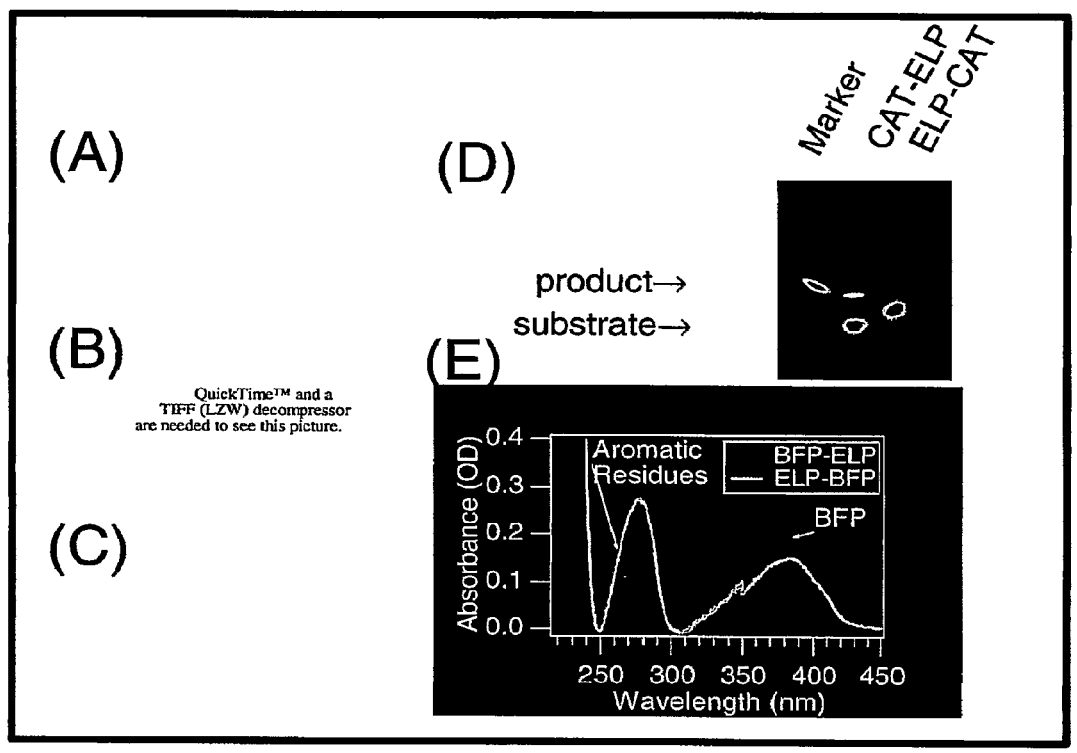
Figure 7. SDS-PAGE of purification of ELP fusion protein in the following orientation.

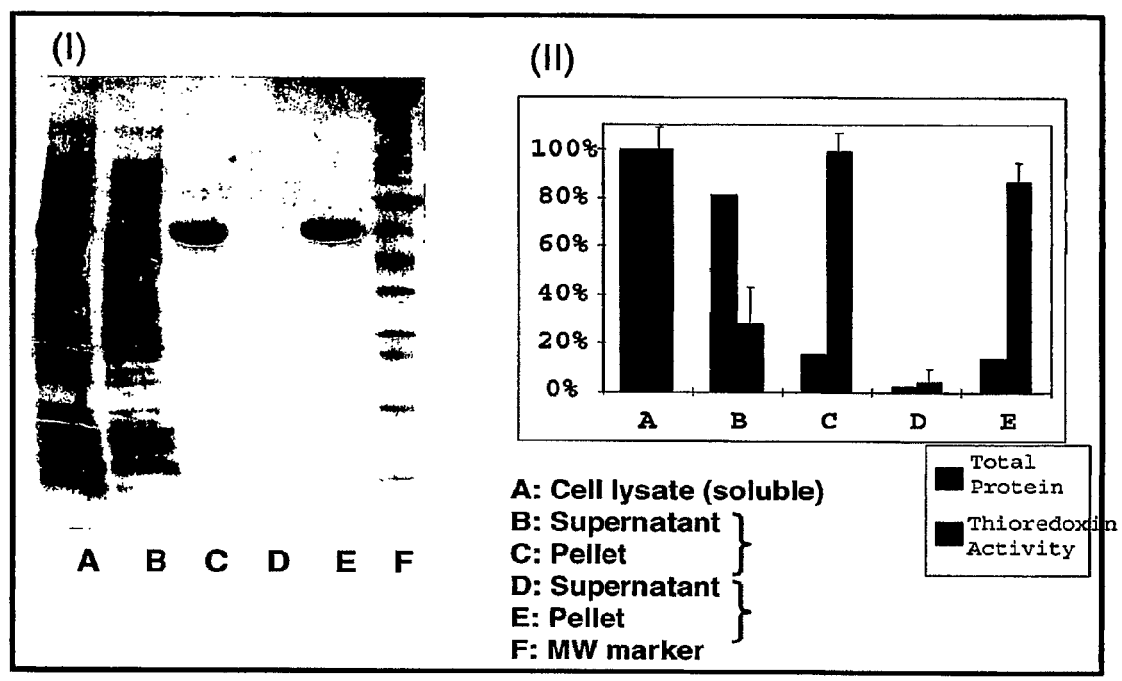
Figure 8. (I) SDS-PAGE characterization of inverse transition purifications, (II) Total protein (green) and thioredoxin (Trx) activity (red) for each stage of purification of the thioredoxin/90-mer ELP.

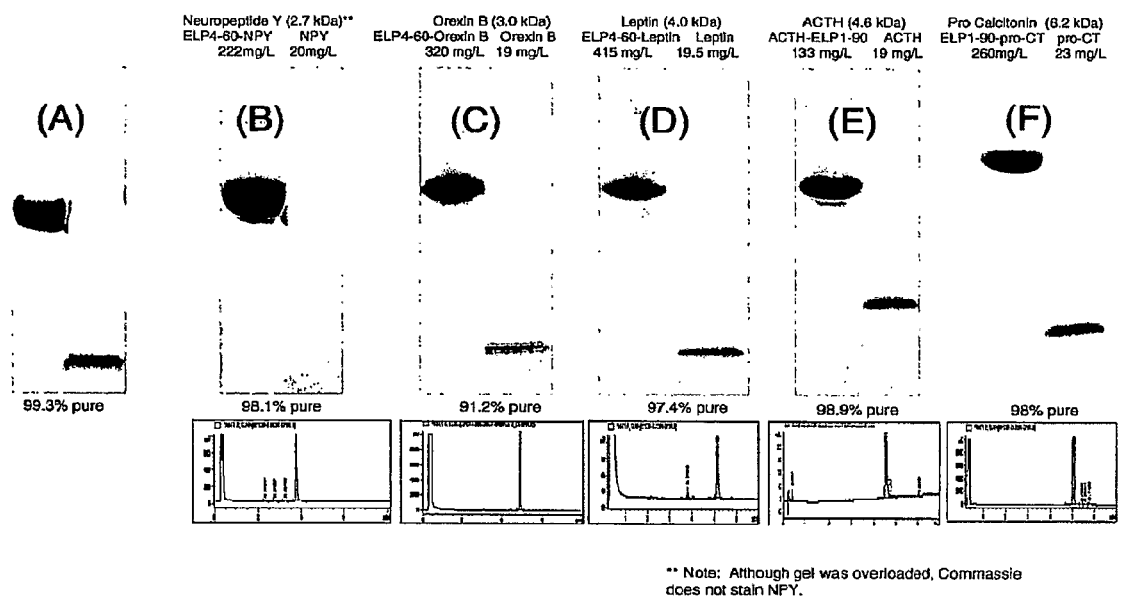
Figure 9. Examples of synthesis of ELP-peptide conjugates, (A) Morphine modulating neurioeptide (MMN), (B) Neuropeptide Y (NPY), (C) Orexin B, (D) Leptin (E) ACTH, (F) Pro-calcitonin.

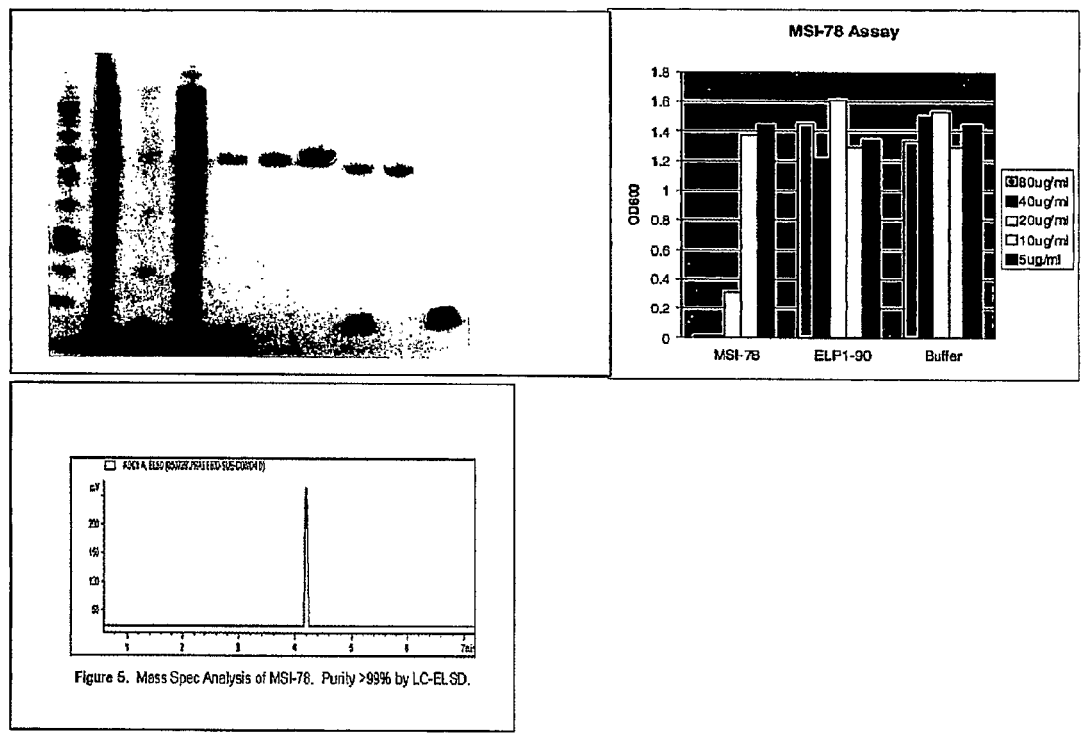
Figure 10. Examples of ELP-peptide conjugate. (A) Purification of ELP1-90-MSI-78 and MSI-78. (B) Purity of EP-MSI-78 conjugate determined by liquid chromatography combined with mass spectrometry.

SEQUENCE LISTING

```
<160> NUMBER OF SEQ ID NOS: 15

<210> SEQ ID NO 1
<211> LENGTH: 5
<212> TYPE: PRT
<213> ORGANISM: Unknown
<220> FEATURE:
<223> OTHER INFORMATION: ELP pentapeptide
<220> FEATURE:
<221> NAME/KEY: REPEAT
<222> LOCATION: (1)..(5)
<223> OTHER INFORMATION: May be repeated
<220> FEATURE:
<221> NAME/KEY: MISC_FEATURE
<222> LOCATION: (4)..(4)
<223> OTHER INFORMATION: Xaa may be any naturally or non-naturally
      occurring amino acid
```

```
<400> SEQUENCE: 1

Val Pro Gly Xaa Gly
1               5

<210> SEQ ID NO 2
<211> LENGTH: 22
<212> TYPE: PRT
<213> ORGANISM: Unknown
<220> FEATURE:
<223> OTHER INFORMATION: Anti-microbial peptide MSI-78

<400> SEQUENCE: 2

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 3
<211> LENGTH: 10
<212> TYPE: PRT
<213> ORGANISM: Unknown
<220> FEATURE:
<223> OTHER INFORMATION: ELP decapeptide
<220> FEATURE:
<221> NAME/KEY: REPEAT
<222> LOCATION: (1)..(10)
<223> OTHER INFORMATION: May be repeated as a whole unit
<220> FEATURE:
<221> NAME/KEY: REPEAT
<222> LOCATION: (1)..(5)
<223> OTHER INFORMATION: May be repeated as a subunit
<220> FEATURE:
<221> NAME/KEY: MISC_FEATURE
<222> LOCATION: (4)..(4)
<223> OTHER INFORMATION: Xaa may be any naturally or non-naturally
      occurring amino acid
<220> FEATURE:
<221> NAME/KEY: REPEAT
<222> LOCATION: (5)..(10)
<223> OTHER INFORMATION: May be repeated as a subunit

<400> SEQUENCE: 3

Val Pro Gly Xaa Gly Val Pro Gly Lys Gly
1               5                   10

<210> SEQ ID NO 4
<211> LENGTH: 4
<212> TYPE: PRT
<213> ORGANISM: Unknown
<220> FEATURE:
<223> OTHER INFORMATION: ELP tetrapeptide

<400> SEQUENCE: 4

Val Pro Gly Gly
1

<210> SEQ ID NO 5
<211> LENGTH: 4
<212> TYPE: PRT
<213> ORGANISM: Unknown
<220> FEATURE:
<223> OTHER INFORMATION: ELP tetrapeptide

<400> SEQUENCE: 5

Gly Gly Val Pro
1
```

```
<210> SEQ ID NO 6
<211> LENGTH: 4
<212> TYPE: PRT
<213> ORGANISM: Unknown
<220> FEATURE:
<223> OTHER INFORMATION: ELP tetrapeptide

<400> SEQUENCE: 6

Gly Gly Phe Pro
1

<210> SEQ ID NO 7
<211> LENGTH: 4
<212> TYPE: PRT
<213> ORGANISM: Unknown
<220> FEATURE:
<223> OTHER INFORMATION: ELP tetrapeptide

<400> SEQUENCE: 7

Gly Gly Ala Pro
1

<210> SEQ ID NO 8
<211> LENGTH: 5
<212> TYPE: PRT
<213> ORGANISM: Unknown
<220> FEATURE:
<223> OTHER INFORMATION: ELP pentapeptide

<400> SEQUENCE: 8

Val Pro Gly Val Gly
1               5

<210> SEQ ID NO 9
<211> LENGTH: 5
<212> TYPE: PRT
<213> ORGANISM: Unknown
<220> FEATURE:
<223> OTHER INFORMATION: ELP pentapeptide

<400> SEQUENCE: 9

Gly Val Gly Val Pro
1               5

<210> SEQ ID NO 10
<211> LENGTH: 5
<212> TYPE: PRT
<213> ORGANISM: Unknown
<220> FEATURE:
<223> OTHER INFORMATION: ELP pentapeptide

<400> SEQUENCE: 10

Gly Lys Gly Val Pro
1               5

<210> SEQ ID NO 11
<211> LENGTH: 5
<212> TYPE: PRT
<213> ORGANISM: Unknown
<220> FEATURE:
<223> OTHER INFORMATION: ELP pentapeptide

<400> SEQUENCE: 11

Gly Val Gly Phe Pro
1               5
```

```
<210> SEQ ID NO 12
<211> LENGTH: 5
<212> TYPE: PRT
<213> ORGANISM: Unknown
<220> FEATURE:
<223> OTHER INFORMATION: ELP pentapeptide

<400> SEQUENCE: 12

Gly Phe Gly Phe Pro
1               5

<210> SEQ ID NO 13
<211> LENGTH: 5
<212> TYPE: PRT
<213> ORGANISM: Unknown
<220> FEATURE:
<223> OTHER INFORMATION: ELP pentapeptide

<400> SEQUENCE: 13

Gly Glu Gly Val Pro
1               5

<210> SEQ ID NO 14
<211> LENGTH: 5
<212> TYPE: PRT
<213> ORGANISM: Unknown
<220> FEATURE:
<223> OTHER INFORMATION: ELP pentapeptide

<400> SEQUENCE: 14

Gly Phe Gly Val Pro
1               5

<210> SEQ ID NO 15
<211> LENGTH: 5
<212> TYPE: PRT
<213> ORGANISM: Unknown
<220> FEATURE:
<223> OTHER INFORMATION: ELP pentapeptide

<400> SEQUENCE: 15

Gly Val Gly Ile Pro
1               5
```

METHODS AND COMPOSITIONS FOR DELIVERING ACTIVE AGENTS WITH ENHANCED PHARMACOLOGICAL PROPERTIES

RELATED APPLICATIONS

This application is a national phase application of PCT Application PCT/US2006/048572, filed Dec. 20, 2006, and published in English on Jun. 28, 2007, as International Publication No. WO 2007/073486, and which claims the benefit of United States Provisional Patent Application Ser. No. 60/751,896, filed Dec. 20, 2005, the disclosure of each of which is incorporated by reference herein in its entirety.

GOVERNMENT FUNDING

This invention was made with Government support under grant number EB00188 and GM-061232 from the National Institutes of Health. The US Government has certain rights to this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PHAS_003_01US_SeqList_ST25.txt, date recorded: Oct. 23, 2009, file size 4 kilobytes).

FIELD OF THE INVENTION

The present invention concerns methods and formulations for improving pharmacological properties of active agents to be delivered to a subject.

BACKGROUND OF THE INVENTION

A significant problem with many candidate drugs, or even drugs in clinical use, is insufficient or unsatisfactory in vivo efficacy. Insufficient in vivo efficacy can be manifested in a variety of ways, such as (i) low bioavailability of the active compound; (ii) undesirably short half-life of the active compound, (iii) and/or undesirably high systemic toxicity of the active compound. To avoid eliminating otherwise promising drugs from clinical use, there remains a need for new approaches to enhancing the in vivo efficacy of active compounds in their delivery to human and animal subjects.

U.S. Pat. No. 6,004,782 to Danielle et al. describes bioelastic polypeptides and the expression thereof in host cells. The use thereof as fusion proteins containing therapeutics is described in a cursory fashion at column 15, lines 43-53 therein. Enhancing the in vivo efficacy of an active agent is neither suggested nor described.

U.S. Pat. No. 6,582,926 to Chilkoti describes, among other things, methods of targeting compounds to regions of interest in a subject by administering the compound to be delivered as a conjugate with a polymer that undergoes an inverse temperature transition (such as an ELP). Compounds to be delivered include certain radionuclides, chemotherapeutic agents, cytotoxic agents, and imaging agents as set forth at column 11, lines 6-21. Enhancing the in vivo efficacy of an active agent is neither suggested nor described.

U.S. Pat. No. 6,852,834 to Chilkoti describes, among other things, fusion proteins that are isolatable by phase transition, primarily to improve the yield thereof during manufacturing. Fusion proteins of therapeutic proteins are generally described at column 11, lines 10-24. Enhancing the in vivo efficacy of an active agent is neither suggested nor described.

SUMMARY OF THE INVENTION

The present invention provides a method of enhancing in vivo efficacy of an active agent, comprising: administering to a subject an active agent that is coupled to a bioelastic polymer or elastin-like peptide, wherein the in vivo efficacy of the active agent is enhanced as compared to the same active agent when administered to the subject not coupled to (or not associated with) a bioelastic polymer or ELP. In vivo efficacy may be enhanced in one, or more, of the following ways: solubility, bioavailability, effective therapeutic dose, formulation compatibility, resistance to proteolysis, half-life of the administered peptide active therapeutic agent, persistence in the body subsequent to administration, and rate of clearance from the body subsequent to administration.

Stated otherwise, the present invention provides a method of delivering an active agent to a subject, comprising: administering to said subject a conjugate of said active agent and an elastin-like peptide; wherein the in vivo efficacy of said active agent is enhanced in said subject when said active agent is administered to said subject in conjugated form as said conjugate as compared to the same amount of said active agent administered to said subject in unconjugated form. In some embodiments, at least one of: (i) the bioavailability of said active agent is greater; (ii) the half-life of said active agent is greater, (iii) the systemic toxicity of said active agent is less, in said subject when said active agent is administered to said subject in conjugated form as said conjugate as compared to the same amount of said active agent administered to said subject in the same way (e.g., the same dosage of active agent, administered in the same vehicle or carrier composition, by the same route of administration) in unconjugated form.

The active agent may be a diagnostic agent, a therapeutic agent, an imaging agent, or a chemotherapeutical agent. In some embodiments the active agent is a (i) small molecule, (ii) radionuclide, (iii) peptide (iv) peptidomimetic, (v) protein, (vi) antisense oligonucleotide, (vii) peptide nucleic acid, (viii) siRNA, (ix) metal chelate, or (x) carbohydrate. In some embodiments the active agent is a protein or peptide. In some embodiments the active agent is an antibody such as a therapeutic or diagnostic antibody.

The conjugate is generally to the subject in a treatment-effective amount by any suitable route, such as parenteral injection.

A further aspect of the present invention is a conjugate as described herein in a pharmaceutically acceptable carrier.

A further aspect of the present invention is the use of an active agent as described herein, in conjugated form as described herein, for carrying out a method as described herein.

The foregoing and other objects and aspects of the invention are explained in greater detail in the drawings herein and the specification set forth below.

BRIEF DESCRIPTION OF THE DRAWINGS

FIG. 1. SDS-PAGE of a library of ELPs that are polymerized at the gene level, expressed in *E. coli*, and purified by exploiting the phase transition of the ELPs.

FIG. 2. SDS-PAGE analysis of (A) $^{14}$C-ELP visualized by copper staining, (B) $^{14}$C-ELP autoradiography after SDS-PAGE. (C) Pharmacokinetic analysis of $^{14}$C-ELP in mice (Balb/c nu/nu) exhibits a characteristic distribution and elimination response with a terminal half-life of 8.4 hr.

FIG. 3. Uptake and localization of an ELP All images are of squamous cell carcinoma (FaDu) cells taken with a LSM-510 laser scanning confocal fluorescence microscope. The cells are incubated with ELP-Alexa488 (green) for 1 hour prior to co-staining. (A) Cells are stained with DiI-CM (red) to label the cell membrane. (B) Cells are co-stained with lysotracker red (red) which selectively stains the lysosomes. The ELP colocalizes with the lysotracker red dye (note the yellow fluorescence).

FIG. 4. (A) Synthesis of a derivative with a terminal maleimide: It shows that a derivative with a terminal maleimide is prepared by attaching a pH sensitive hydrazone linker to Doxorubicin (hereinafter as Dox), a cancer chemotherapeutic agent at the 13-keto position. Then, the terminal maleimide of the derivative is conjugated to an ELP, which presents one or more Cysteine residues. (B) It is an example of cytotoxicity of Doxorubicin conjugated to ELP2-160JM2 conjugate (hereinafter as ELP-Dox) in a MTT cell viability assay. The cytotoxicity of ELP-Doxorubicin and unconjugated Dox is a function of the equivalent Doxorubicin concentration. Compared to the free drug, ELP-Doxorubicin demonstrates almost equivalent cytotoxicity of the free drugs. (C) ELP-Dox and Dox are injected at the same concentration into mice via tail vein injections. After 1 h, no Dox can be detected from the blood samples of the mice. However, ~20 injected gram/g serum (% ID/g) is detected from the mice injected with ELP-Dox. The result of this experiment demonstrates that the conjugated form has a greater plasma half-life of the drug. (D) It demonstrates the biodistribution of Dox and ELP-Dox injected nude mice with human tumor xenografts. Upon conjugation of Dox to ELP, a different pattern of distribution is obtained. The concentrations of Dox in the heart; liver and lung are greater than those of ELP-OPDX, however, the concentration of ELP-Dox in tumor is greater than that of Dox.

FIG. 5. Accumulation of $^{14}C$-labeled ELPs in tumors. The two ELPs reported are a thermally sensitive ELP1 and a thermally insensitive ELP2 in tumors that are either heated to 41.5° C. or not heated.

FIG. 6. Expression of different ELP fusion proteins as examples of recombinant ELP-protein conjugates. All ELP-protein conjugates are prepared by fusion of the gene of the protein, ELP and expression in a heterogeneous expression system (e.g., E coli). The left panel shows examples of blue fluorescent protein (BFP), chloramphenicol acetyl transferase (CAT) and Kringle1-3 domains (K1-3: angiostatin). The right panel shows other examples of purified ELP-protein conjugates.

FIG. 7. SDS-PAGE of purification of ELP fusion protein in the following orientation: The preparation of the protein-ELP and ELP-protein shows that protein conjugates of ELPs can be synthesized in either orientation. (A) CAT, (B) BFP, ©(C) Trx. (D) Thin layer chromatography showing activity of CAT, (D) Fluorescence of BFP-ELP n ELP-BFP showing functionality of BDFP in the fusion.

FIG. 8. (I) SDS-PAGE characterization of inverse transition purifications: It shows each stage of purification for the thioredoxin/90-mer ELP fusion (49.9 kDa, lanes 1 through 5) Lane A: soluble lysate; lane B: discarded supernatant containing contaminating E. coli proteins; lane 3: resolubilized pellet fraction containing purified fusion protein, lane 4, second round supernatant; lane 5: second round pellet; lane 6: molecular weight markers (kDa). (II) Total protein (green) and thioredoxin (Trx) activity (red) for each stage of purification of the thioredoxin/90-mer ELP. Values are normalized to those determined for the soluble lysate.

FIG. 9. Examples of synthesis of ELP-peptide conjugates. All conjugates are prepared recombinantly as fusions with ELP. The two lanes in each SDS-PAGE gels from A-F show the fusion (conjugate) on left, and the peptide on right. Mass spectrometry results for each purified peptide are shown below the SDS-PAGE gels. (A) Morphine modulating neuropeptide (MMN), (B) Neuropeptide Y (NPY), (C) Orexin B, (D) Leptin (E) ACTH, (F) Pro-calcitonin.

FIG. 10. Examples of ELP-peptide conjugate. Recombinant fusion of antimicrobial peptide MSI-78 with ELP (ELP-peptide conjugate). Sequence of MSI-78: Sequence=GIGKFLKKAKKFGKAFVKILKK (SEQ ID NO.: 2). (A) Purification of ELP 1-90-MSI-78 and MSI-78. SDS-Page gel shows both high purity of the conjugate and the peptide produced recombinantly. (B) Purity of EP-MSI-78 conjugate determined by liquid chromatography combined with mass spectrometry. One compound was detected with a molecular weight of 2476.6 and purity is >99% by LC-ELSD (C) Bactericidal activity of MSI-78.

DETAILED DESCRIPTION OF THE PREFERRED EMBODIMENTS

The disclosures of all United States patent references cited herein are to be incorporated by reference herein in their entirety.

"Active agent" as used herein may be any suitable active agent, including therapeutic and diagnostic or imaging agents.

Examples of imaging agents include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), MRI contrast agents (e.g., Gadolinum chelates (Gd)) luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody.

"Therapeutic agent" as used herein may be any suitable therapeutic agent, including but not limited to radionuclides, chemotherapeutic agents; cytototoxic agents, parathyroid hormone related protein (parathyroid hormone related protein), growth hormone (GH) particularly human and bovine growth hormone, growth hormone-releasing hormones; interferon including α-, β-, or γ-interferons, etc, interleukin-I; interleukin-II; erythropoietin including α- and β-erythropoietin (EPO), granulocyte colony stimulating factor (GCSF), granulocyte macrophage colony stimulating factor (GM-CSF), anti-angiogenic proteins (e.g., angiostatin, endostatin) PACAP polypeptide (pituitary adenylate cyclase activating polypeptide), vasoactive intestinal peptide (VIP), thyrotrophin releasing hormone (TRH), corticotrophin releasing hormone (CRH), vasopressin, arginine vasopressin (AVP), angiotensin, calcitonin, atrial naturetic factor, somatostatin, adrenocorticotropin, gonadotropin releasing hormone, oxytocin, insulin, somatotropin, HBS antigen of hepatitis B virus, plasminogen tissue activator, coagulation factors including coagulation factors VIII and IX, glucosylceramidase, sargramostim, lenograstin, filgrastin, interleukin-2, dornase-α, molgramostim, PEG-L-asparaginase, PEG-adenosine deaminase, hirudin, eptacog-α (human blood coagulation factor VIIa) nerve growth factors, transforming growth factor, epidermal growth factor, basic fibroblast growth factor, VEGF; heparin including low molecular weight heparin, calcitonin; atrial naturetic factor; antigens; monoclonal antibodies; somatostatin; adrenocorticotropin, gonadotropin releasing hormone; oxytocin; vasopressin; cromolyn sodium; vancomycin; desferrioxamine (DFO); parathyroid hormone, anti-microbials, antifungals, an immunogen or antigen, an antibody such as a monoclonal antibody, or any combination thereof. See, e.g., U.S. Pat. Nos. 6,967,028; 6,930,090; and 6,972,300.

Example therapeutic agents include all of the therapeutic agents set forth in paragraphs 0065 through 0388 of W. Hunter, D. Gravett, et al., US Patent Application Publication No. 20050181977 (Published Aug. 18, 2005) (assigned to Angiotech International AG) the disclosure of which is incorporated by reference herein in its entirety.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb. Radionuclides may also be those useful for delivering a detectable dosage for imaging or diagnostic purposes, even where those compounds are not useful for therapeutic purposes.

"Chemotherapeutic agent" as used herein includes but is not limited to methotrexate, daunomycin, mitomycin, cisplatin (cisplatinum or cis-dianminedichloroplatinum (II) (CCDP)), vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamoxifen, paclitaxel, vincristine, vinblastine, camptothecin, actinomycin D, and cytarabine, combrestatin and its derivatives.

"Cytotoxic agent" as used herein includes but is not limited to ricin (or more particularly the ricin A chain), aclacinomycin, diphtheria toxin, Monensin, Verrucarin A, Abrin, Vinca alkaloids, Tricothecenes, and *Pseudomonas* exotoxin A.

"Immunogen" and "antigen" are used interchangeably and mean any compound to which a cellular or humoral immune response is to be directed against, and include bacterial antigens, viral antigens, and tumor antigens. Non-living immunogens (e.g., killed immunogens, subunit vaccines, recombinant proteins or peptides or the like) are currently preferred. Examples of suitable immunogens include those derived from bacterial surface polysaccharides which can be used in carbohydrate-based vaccines. Bacteria typically express carbohydrates on their cell surface as part of glycoproteins, glycolipids, O-specific side chains of lipopolysaccharides, capsular polysaccharides and the like. Exemplary bacterial strains include *Streptococcus pneumonia, Neisseria meningitidis, Haemophilus influenza, Klebsiella* spp., *Pseudomonas* spp., *Salmonella* spp., *Shigella* spp., and Group B streptococci. A number of suitable bacterial carbohydrate epitopes which may be used as the immunogen in the present invention are described in the art (e.g., Sanders, et al. Pediatr. Res. 37:812-819 (1995); Bartoloni, et al. Vaccine 13:463-470 (1995); Pirofski, et al., Infect. Immun. 63:2906-2911 (1995) and International Publication No. WO 93/21948) and are further described in U.S. Pat. No. 6,413,935. Exemplary viral antigen or immunogen includes those derived from HIV (e.g., gp120, nef, tat, pol). Exemplary fungal antigens include those derived from *Candida albicans, Cryptococcus neoformans, Coccidoides* spp., *Histoplasma* spp., and *Aspergillus* spp. Parasitic antigens include those derived from *Plasmodium* spp., *Trypanosoma* spp., *Schistosoma* spp., *Leishmania* spp. and the like. Exemplary carbohydrate epitopes that may be utilized as antigens or immunogens in the present invention include bur are not limited to the following: Galα1,4Galβ- (for bacterial vaccines); GalNAcα-(for cancer vaccines); Manβ1,2(Manβ)$_n$Manβ-(for fungal vaccines useful against, for example, *Candida albicans*), where n=O→∞; GalNAcβ1, 4(NeuAcα-2,3)Galβ1,4Glcβ-O-ceramide. (for cancer vaccines); Galα1,2(Tyvα1,3)Manα1,4Rhaα1,3 Galα1,2(Tyα1,3)Manα4Rha- and Galα1,2(Abeα1,3)Manα1,4Rhaα1,3 Galα1,2(Abeα1,3)Manα1,4Rhaα1,3Galα1,2 (Abeα1,3) Manα1,4Rha-(both of which are useful against, for example, *Salmonella* spp.). Carbohydrate epitopes as antigens or immunogens and the synthesis thereof are described further in U.S. Pat. No. 6,413,935. In one embodiment the immunogen may be an anthrax immunogen; i.e. an immunogen that produces protective immunity to *Bacillus anthracis*, such as anthrax vaccine, A, (Michigan Department of Health, Lansing, Mich.; described in U.S. Pat. No. 5,728,385). Other examples of immunogens or antigens include but are not limited to those that produce an immune response or antigenic response to the following diseases and disease-causing agents: adenoviruses; *Bordetella pertussus*; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; Globulin; *haemophilus influenza* type b; *Haemophilus influenzae; Haemophilus pertussis; Helicobacter pylori; Hemophilus*; hepatitis; hepatitis A; hepatitis B; Hepatitis C; herpes viruses; HIV; HIV-1 viruses; HIV-2 viruses; HTLV; Influenza; Japanese encephalitis; Klebsiellae species; *Legionella pneumophila; leishmania*; leprosy; lyme disease; malaria immunogen; measles; meningitis; meningococcal; Meningococcal Polysaccharide Group A; Meningococcal Polysaccharide Group C; mumps; Mumps Virus; mycobacteria and; *Mycobacterium tuberculosis; Neisseria; Neisseria gonorrhoeae; Neisseria meningitidis*; ovine blue tongue; ovine encephalitis; papilloma; parainfluenza; paramyxovirus; paramyxoviruses; Pertussis; Plague; Pneumococcus; *Pneumocystis carinii*; Pneumonia; Poliovirus; Proteus species; *Pseudomonas aeruginosa*; rabies; respiratory syncytial virus; rotavirus; Rubella; Salmonellae; schistosomiasis; Shigellae; simian immunodeficiency virus; Smallpox; *Staphylococcus aureus; Staphylococcus* species; *Streptococcus pneumoniae; Streptococcus pyogenes; Streptococcus* species; swine influenza; tetanus; *Treponema pallidum*; Typhoid; Vaccinia; varicella-zoster virus; and *Vibrio cholerae*. The antigens or immunogens may, include various toxoids, viral antigens and/or bacterial antigens such as antigens commonly employed in the following vaccines: chickenpox vaccine; diphtheria, tetanus, and pertussis vaccines; *haemophilus influenzae* type b vaccine (Hib); hepatitis A vaccine; hepatitis B vaccine; influenza vaccine; measles, mumps, and rubella vaccines (MMR); pneumococcal vaccine; polio vaccines; rotavirus vaccine; anthrax vaccines; and tetanus and diphtheria vaccine (Td). See, e.g., U.S. Pat. No. 6,309,633. Antigens or immunogens that are used to carry out the present invention include those that are derivatized or modified in some way, such as by conjugating or coupling one or more additional groups thereto to enhance function or achieve additional functions such as targeting or enhanced delivery thereof, including but not limited to those techniques described in U.S. Pat. No. 6,493,402 to Pizzo et al. (α-2 macroglobulin complexes); U.S. Pat. Nos. 6,309,633; 6,207,157; 5,908,629, etc.

Interferon (IFNs) are used herein refers to natural proteins produced by the cells of the immune system of most vertebrates in response to challenges by foreign agents such as viruses, bacteria, parasites and tumor cells, and its function is to inhibit viral replication within other cells. Interferons belong to the large class of glycoproteins known as cytokines. Three major classes of interferons for human have been discovered as type I, type II and type III, classified according to the type of receptor through which they signal. Human type I IFNs comprise a vast and growing group of IFN proteins, designated IFN-α, IFN-β, IFN-κ, IFN-δ, IFN-ε, IFN-τ, IFN-ω and IFN-ζ. [See Interferon-ζ/limitin: Novel type I Interferon that displays a narrow range of biological activity, Oritani Kenji and Tomiyama Yoshiaki, *International Journal of hematology,* 2004, 80, 325-331; Characterization of the type I interferon locus and identification of novel genes, Hardy et al., *Genomics,* 2004, 84, 331-345.] Homologous molecules to type I IFNs are found in many species, including most mammals, and some have been identified in birds, reptiles, amphibians and fish species. [See The interferon system of non-mammalian vertebrates, Schultz et al., *Developmental and Comparative Immunology,* 28, 499-508.] All type I IFNs bind to a specific cell surface receptor complex known as the IFN-α receptor (IFNAR) that consists of IFNAR1 and IFNAR2 chains. The type II IFNs only has one member called IFN-γ. Mature IFN-γ is an anti-parallel homodimer, which binds to the IFN-γ receptor (IFNGR) complex to elicit a signal within its target cell. The type III IFN group consists of three IFN-γ molecules called IFN-λ1, IFN-λ2 and IFN-λ3 (also called IL29, IL28A and IL28B respectively). [See Novel interferons, Jan Vilcek, *Nature Immunology,* 2003, 4, 8-9.] The IFN-λ molecules signal through a receptor complex consisting of IL10R2 (also called CRF2-4) and IFNLR1 (also called CRF2-12). [See Murine interferon lambdas (type III interferons) exhibit potent antiviral activity in vivo in a poxvirus infection model, Bartlett et al., *Journal of General Virology,* 2005, 86, 1589-1596.]

"Antibody" or "antibodies" as used herein refers to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, or human, or may be humanized or chimeric antibodies. The term "antibody" as used herein includes antibody fragments which retain the capability of binding to a target antigen, for example, Fab, $F(ab')_2$, and Fv fragments, and the corresponding fragments obtained from antibodies other than IgG. Such fragments are also produced by known techniques. Antibodies may be for diagnostic purposes or for therapeutic purposes. Examples of therapeutic antibodies include but are not limited to herceptin, rituxan, campath (Mellinium pharma Inc.), gemtuzumab (Cell tech.), herceptin (Genentech), panorex (Centocor GSK), rituximab (Genentech), bexxar (Coraxia GSK), edrecolomab (Glaxowellcome), alemtuzumab (ILEX Pharmaceuticals), mylotrag (Whety-Ayerst), IMC-C225, smartin 195, and mitomomab (Imclone systems). Therapeutic antibodies include those coupled to a therapeutic compound and "cold dose" antibodies, such as for reducing non-specific binding. See, e.g., Abrams et al., U.S. Pat. No. RE38,008.

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms." to any type of treatment that imparts a benefit to a patient afflicted with a disease, including improvement in the condition of the patient (e.g., in one or more symptoms), delay in the progression of the disease, etc.

"Treatment effective amount" as used herein means an amount of the antibody sufficient to produce a desirable effect upon a patient inflicted with a condition such as cancer, diabetes, bacterial or viral infection, etc., including improvement in the condition of the patient (e.g., in one or more symptoms), delay in the progression of the disease, etc. With an immunogen a "treatment effective amount" may be an amount effective to produce an immune response or protective immunity (in whole or in part) against subsequent infection by a bacterial, viral, fungal, protozoal, or other microbial agent.

"Conjugate" as used herein refers to two or more moieties or functional groups that are covalently or noncovalently joined to one another, such that the two or more groups function together as a single structure under the conditions of the methods described herein. In one embodiment, the conjugate is a fusion protein. In some embodiments, the conjugate refers to the two moieties that are chemically or enzymatically attached to each other.

"Fusion protein" as used herein refers to a protein or peptide, produced by recombinant means (i.e., expression from a nucleic acid) that is comprised of a first protein or peptide covalently joined on expression to a second protein or peptide.

A "polymer that undergoes an inverse temperature transition" herein refers to a polymer that is soluble in an aqueous solution at a lower temperature, and is insoluble in an aqueous solution at a higher temperature.

"Transition temperature" or "$T_t$" as used herein, refers to the temperature above which a polymer that undergoes an inverse temperature transition is insoluble in an aqueous system (e.g., water, physiological saline solution), and below which such a polymer is soluble in an aqueous system.

A "bioelastic polymer" is, in general, a polypeptide that exhibits an inverse temperature transition. Bioelastic polymers are discussed in greater detail below. Such bioelastic polymers are typically elastin-like peptides.

While the present invention is concerned primarily with the treatment of human subjects, the invention may also be used for the treatment of animal subjects, particularly mammalian subjects such as dogs, cats, horses, cows, pigs, etc., for veterinary purposes.

Subjects in need of treatment by the methods described herein include subjects afflicted with any disorder conventionally or currently treated or diagnosed by the active agents described herein, including but not limited to subjects afflicted with solid tumors or cancers such as lung, colon, breast, brain, liver, prostate, spleen, muscle, ovary, pancreas, skin (including melanoma) etc; subjects afflicted with or at risk of developing a viral, bacterial, protozoal, or other microbial infection; etc.

Bioelastic polymers. Bioelastic polymers are known and described in, for example, U.S. Pat. No. 5,520,672 to Urry et al. In general, bioelastic polymers are polypeptides comprising elastomeric units of bioelastic pentapeptides, tetrapeptides, and/or nonapeptides (that is, "elastin-like peptides"). Thus in some embodiments the elastomeric unit is a pentapeptide, in other embodiments the elastomeric unit is a tetrapeptide, and in still other embodiments the elastomeric unit is a nonapeptide. Bioelastic polymers that may be used to carry out the present invention are set forth in U.S. Pat. No. 4,474,851, which describes a number of tetrapeptide and pentapeptide repeating units that can be used to form a bioelastic polymer. Specific bioelastic polymers that can be used to carry out the present invention are also described in U.S. Pat. Nos. 4,132,746; 4,187,852; 4,500,700; 4,589,882; and 4,870,055. Still other examples of bioelastic polymers are set forth in U.S. Pat. No. 6,699,294 to Urry, U.S. Pat. No. 6,753,311 to Fertala and Ko; and U.S. Pat. No. 6,063,061 to Wallace.

In one embodiment, the bioelastic polymers used to carry out the present invention are polypeptides of the general formula (VPGXG)$_m$ (SEQ ID NO.: 1), where X is any amino acid (e.g., Ala, Leu, Phe) and m is any suitable number such as 2, 3 or 4 up to 60, 80 or 100 or more. The frequency of the various amino acids as the fourth amino acid can be changed, as well as the frequency of X. For example, the bioelastic polymers used to carry out the present invention may be polypeptides of the general formula: [(VPGXG)$_m$ (VPGKG)$_n$]$_o$ (SEQ ID NO.: 3), where m is 2, 3 or 4 to 20 or 30, n is 1, 2 or 3, o is at least 2, 3 or 4 up to 30, 40 or 50 or more. Any ratios of X/K can be possible, which means where m is 1, 2, or 3 up to 100, 150, or 300 or more, n is 1, 2 or 3 up to 100 or 150 or 300 or more, o is at least 1, 2, or 3 up to 100, 150 or 300 or more.

For example, bioelastic polymers used to carry out the present invention may comprise repeating elastomeric units selected from the group consisting of bioelastic pentapeptides and tetrapeptides, where the repeating units comprise amino acid residues selected from the group consisting of hydrophobic amino acid and glycine residues and where the repeating units exist in a conformation having a beta-turn of the formula:

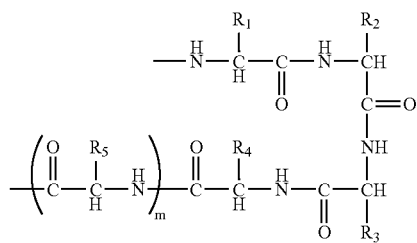

wherein R$_1$-R$_5$ represent side chains of amino acid residues 1-5, and m is 0 when the repeating unit is a tetrapeptide or 1 when the repeating unit is a pentapeptide. Nonapeptide repeating units generally consist of sequential tetra- and pentapeptides. Preferred hydrophobic amino acid residues are selected from the group consisting of alanine, valine, leucine, isoleucine, proline, phenylalanine, tryptophan, and methionine. In many cases, the first amino acid residue of the repeating unit is a residue of valine, leucine, isoleucine or phenylalanine; the second amino acid residue is a residue of proline; the third amino acid residue is a residue of glycine; and the fourth amino acid residue is glycine or a very hydrophobic residue such as tryptophan, phenylalanine or tyrosine. Particular examples include the tetrapeptide Val-Pro-Gly-Gly (SEQ ID NO.: 4), the tetrapeptide GGVP (SEQ ID NO.: 5), the tetrapeptide GGFP (SEQ ID NO.: 6), the tetrapeptide GGAP (SEQ ID NO.: 7), the pentapeptide is Val-Pro-Gly-Val-Gly (SEQ ID NO.: 8), the pentapeptide GVGVP (SEQ ID NO.: 9), the pentapeptide GKGVP (SEQ ID NO.: 10), the pentapeptide GVGFP (SEQ ID NO.: 11), the pentapeptide GFGFP (SEQ ID NO.: 12), the pentapeptide GEGVP (SEQ ID NO.: 13), the pentapeptide GFGVP (SEQ ID NO.: 14), and the pentapeptide GVGIP (SEQ ID NO.: 15). See, e.g., U.S. Pat. No. 6,699,294 to Urry.

Coupling of conjugates may be carried out by any suitable means, including chemical and recombinant means. Chemical or enzymatic coupling may be carried out by procedures known in the art. (See, e.g., U.S. Pat. Nos. 6,930,090; 6,913,903; 6,897,196; and 6,664,043). Coupling of conjugates by recombinant means (e.g., where elastin is joined to a protein or peptide such as an interleukin, by recombinant means such as by expression of a fusion protein) may also be carried out by procedures known in the art (See, e.g., U.S. Pat. Nos. 6,974,572; 6,972,322; 6,962,978; and 6,956,112).

Formulations and administration. Administering of the conjugate to the subject may be carried out by any suitable means, such as subcutaneous injection, intraperitoneal injection, intravenous injection, intramuscular injection, intratumoral, oral administration, inhalation administration, transdermal administration, etc. Preferred administration techniques are typically "systemic" in that a particular region of interest is not specifically targeted.

The conjugates (or "active compounds") described above may be formulated for administration in a single pharmaceutical carrier or in separate pharmaceutical carriers for the treatment of a variety of conditions. In the manufacture of a pharmaceutical formulation according to the invention, the active compounds including the physiologically acceptable salts thereof, or the acid derivatives of either thereof are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy, which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder. Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. Suitable formulations comprise citrate or bis.backslash.tris buffer (pH 6) or ethanol/water and contain from 0.1 to 0.2M active ingredient. The therapeutically effective dosage of any one active agent, the use of which is in the scope of present invention, will vary somewhat from compound to compound, patient to patient, and will depend upon factors such as the condition of the patient and the route of delivery; Such dosages can be determined in accordance with routine pharmacological procedures known to those skilled in the art, particularly in light of the disclosure provided herein. In one example, the dosage is from 1 to 10 micrograms of active compound per Kilogram subject body weight.

In another example, where the therapeutic agent is $^{131}$I, the dosage to the patient is typically from 10 mCi to 100, 300 or even 500 mCi. Stated otherwise, where the therapeutic agent is $^{131}$I, the dosage to the patient is typically from 5,000 Rads to 100,000 Rads (preferably at least 13,000 Rads, or even at least 50,000 Rads). Doses for other radionuclides are typically selected so that the tumoricidal dose is equivalent to the foregoing range for $^{131}$I.

In a preferred embodiment, the improved pharmacological properties of the invention are utilized to improve the delivery and/or dosage regime to the subject. For example, an improved half live of the active agent is utilized to reduce the frequency of dosages to the patient (e.g., one dosage or administration every three or four days; more preferably one administration per week, still more preferably one administration every two weeks; still more preferably one administration per month); an improved bioavailability is utilized to reduce the overall dosage of the active agent administered to the patient, etc.

The present invention is explained in greater detail in the following non-limiting examples.

EXAMPLES

The goal of this invention is to selectively deliver drugs or imaging agents to diseased sites in order to improve therapeutic efficacy and limit systemic toxicity.

The invention has four parts:

1. Drug or Imaging Agent carriers: The carrier is a novel macromolecular drug carrier, consisting of elastin-like polypeptides (ELPs). ELPs belong to a unique class of biopolymers that undergo an inverse temperature phase transition; they are soluble at temperatures below their transition temperature ($T_t$) but become insoluble and aggregate at temperatures above their $T_t$[1-3].

(i) The ELP may be designed with a $T_t$ that is below the local temperature at the diseased site so that it will aggregate at the diseased site.
  (ii) Alternatively the ELP may be designed to have a $T_t$ that is above the diseased site so as to remain in soluble form
  (iii) The ELP may contain sites for the covalent or enzymatic attachment of drugs or imaging agents or targeting moieties.
  (iv) The ELP may also be designed to contain genetically encodable targeting moieties (one or more) such as a peptide or protein to specifically target the ELP to the diseased site or organ.

2. Definition of
  (A) Drug: Any molecule that has therapeutic value against any disease.
  (B) Imaging agent: Any molecule that provides visualization of the diseased site or organ Example of the drug or imaging agent would include, though not exclusively: (i) small molecule, (ii) radionuclide, (iii) peptide (iv) peptidomimetic, (v) protein, (vi) antisense oligonucleotide, (vii) peptide nucleic acid, (viii) siRNA, (ix) metal chelate, (x) carbohydrates.

3. Attachment or association of drug or imaging agent. The drug can be covalently linked to the ELP through a stable or labile linkage scheme. The drug may be hydrophobically associated with the ELP. The drug may be attached to the ELP through a chelation method. The drug may be associated with the ELP through molecular recognition through secondary bonds. The drug may also be attached to the ELP through the action of an enzyme. In the case of molecules such as peptides proteins that can be produced recombinantly, the ELP and drug may be produced as a single entity in suitable host (*E. coli, pichia pastoris*, mammalian cells, or baculovirus) from a synthetic or cloned gene. The "ELP-drug/imaging agent conjugate" may be synthesized so that the link between the conjugate may be stable so as to deliver the single entity as a therapeutic or imaging agent or designed to be labile under the action of pH or light, or the action of enzymes to liberate the drug from the ELP.

4. Administration: The ELP-drug conjugate or fusion protein will be: (i) injected into the subject systemically (iv, ia, ip or im) (ii) locally into the diseased site or organ, (iii) or delivered orally, or (iv) parenterally.

The injected ELP-drug/imaging agent conjugate or fusion protein will exhibit as compared to the free drug one or more of the following: (1) enhanced solubility of the drug/imaging agent in its conjugated form over free drug/imaging agent, increased circulation half-life, exhibit reduced clearance from the body, or increased bioavailability of the drug/imaging agent, resulting in reduced dose and frequency of injection, an improved therapeutic index or improved visualization of the diseased site or organ.

Examples

Synthesis and Characterization of ELPs. ELPs are typically prepared by a recombinant synthesis in *E. coli*. However, other hosts may be used for recombinant synthesis as well. ELP may also be prepared by a chemical synthesis. In a typical example of a recombinant synthesis, the polymerization process is carried out at the gene level by a method called recursive directional ligation (RDL), in which a synthetic gene for a repeat sequence for the ELP (typically encoding ~10 pentapeptides of VPGXG (SEQ ID NO.: 1)) are ligated in a head-to-tail manner recursively. After n rounds of ligation into a plasmid, this provides a library of n+1 ELP genes, all of which encode the same peptide sequence, but with MWs that are multiples of the drug.

ELP-drug conjugation. An ELP containing a unique C-terminal cysteine residue is synthesized and purified by inverse transition cycling (ITC) and conjugated to Doxorubicin molecules through four different pH-sensitive, maleimide-activated, hydrazone linkers. The linkers' structures or length have little effect on the $T_t$ of the ELP-Doxorubicin conjugates, since all conjugates' $T_t$s are similar to those of the native ELP (data not shown). However, the ELP-Doxorubicin conjugates with longer linkers exhibits slower transition kinetics than the ELP-Doxorubicin conjugates with shorter linkers. At pH 4, the release of Doxorubicin from the ELP-Doxorubicin conjugate with the shortest linker reached almost 80% over 72 h.

Cytotoxicity of ELP-Doxorubicin Conjugates. An acid-labile ELP-Doxorubicin conjugate is tested for cytotoxicity in an in vitro cell culture assay with FaDu cells. The unconjugated ELP, the control conjugate, does not show any inherent cytotoxicity, and thus it indicates that ELPs are non-toxic despite of substantial internalization (FIG. 4). By contrast, the ELP-Doxorubicin conjugate shows substantial cytotoxicity during either 24 or 72 h, and the level of toxicity is similar to those of an equivalent Doxorubicin concentration. Accumulation of ELPs in Solid Tumors. Biodistribution studies are carried out by systematically injecting $^{14}$C-labeled ELP into nude mice bearing a FaDu solid carcinoma. The accumulation of the ELPs in implanted tumors is in the range of 10-20% injected dose per gram (% ID/g). When an ELP with a $T_t$ of ~40° C. is systematically injected into a mice and implanted tumors are heated to 42° C., the accumulation is ~20% ID/g. By contrast, when the same ELP is injected without heating the tumors, the accumulation was ~10% ID/g. This data shows that a significant concentration (% ID/g) of the radiolabeled ELP localized in the tumor even when the tumor is not heated. By contrast, the injection of a small radiolabeled molecule (molecular weight<500 Da) in unconjugated form results in significantly lower accumulation in the tumor. This example demonstrates that ELPs can result in significant localization in a diseased site.

TABLE 1

List of ELP-protein conjugates synthesized recombinantly (ELP fusion proteins), molecular weight (MW) of the target proteins, and their yield from a 1 Liter shaker flask culture of *Escherichia coli*.

| Target Proteins | MW (kDa) | Yield (mg/L) |
| --- | --- | --- |
| Angiostatin (K1-3) | 30.7 | 27 |
| Blue fluorescent protein (BFP) | 26.9 | 100 |
| Calmodulin (CalM) | 16.7 | 75 |
| Chloramphenicol acetyltransferase (CAT) | 25.7 | 80 |
| Green fluorescent protein (GFP) | 26.9 | 78-1600 |
| Interleukin 1 receptor antagonist (IL1rRa) | 17.0 | 50 |
| Luciferase | 60.8 | 10 |
| Tissue transglutaminase (tTg) | 77.0 | 36 |
| Tendamistat | 7.9 | 22 |
| Thioredoxin (Trx) | 11.7 | 120 |

TABLE 2

Yield of peptide-ELP conjugates synthesized recombinantly in *E. coli*. Both yield of the conjugate (fusion) and the target peptide is shown, as well as purity as determined by mass spectrometry.

| Peptide | MW (kDa) | Yield Fusion (mg/L culture) | Yield Peptide (mg/L culture) | Purity |
| --- | --- | --- | --- | --- |
| Morphine Modulating Neuropeptide (MMN) | 2.0 | 224 | 17 | 99% |
| Neuropeptide Y (NPY) | 2.7 | 222 | 20 | 98% |
| Orexin B | 3.0 | 320 | 19 | 91% |
| Leptin | 4.0 | 415 | 19 | 97% |
| ACTH | 4.6 | 133 | 19 | 99% |
| Calcitonin | 6.2 | 260 | 23 | 98% |

The foregoing is illustrative of the present invention, and is not to be construed as limiting thereof. The invention is defined by the following claims, with equivalents of the claims to be included therein.

That which is claimed is:

1. A pharmaceutical formulation comprising a therapeutically effective amount of a recombinant fusion protein between vasoactive intestinal peptide (VIP) and an elastin-like peptide (ELP), wherein the formulation is an aqueous preparation for systemic administration, and wherein the ELP comprises an amino acid sequence of the formula (VPGXG)m (SEQ ID NO: 1), where X is an independently selected amino acid and m is 100 or greater.

2. The formulation of claim 1, wherein the VIP is enhanced for its therapeutically effective dose and/or half-life in circulation.

3. The formulation of claim 1, wherein the ELP comprises VPGVG repeats (SEQ ID NO: 8).

4. The formulation of claim 1, wherein the ELP has a transition temperature of about 40° C. in physiological solution.

5. The formulation of claim 1, formulated for subcutaneous injection, intravenous injection, or intramuscular injection.

6. The formulation of claim 1, wherein the recombinant fusion protein does not have a linkage between the VIP and ELP that is labile by enzymatic action.

* * * * *